US010599938B2

(12) United States Patent
Shemesh (10) Patent No.: US 10,599,938 B2
(45) Date of Patent: *Mar. 24, 2020

(54) DETECTION, CHARACTERIZATION AND PRESENTATION OF ADVERSE AIRBORNE PHENOMENA

(71) Applicant: NICARNICA AVIATION AS, Lysaker (NO)

(72) Inventor: Ariel Shemesh, Haifa (IL)

(73) Assignee: NICARNICA AVIATION AS, Lysaker (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/137,094

(22) Filed: Sep. 20, 2018

(65) Prior Publication Data
US 2019/0026580 A1  Jan. 24, 2019

Related U.S. Application Data

(63) Continuation of application No. 15/557,398, filed as application No. PCT/IL2016/050255 on Mar. 8, 2016, now Pat. No. 10,089,547.

(30) Foreign Application Priority Data

Mar. 12, 2015 (IL) .......................................... 237717

(51) Int. Cl.
*G06K 9/20* (2006.01)
*G01W 1/08* (2006.01)
(Continued)

(52) U.S. Cl.
CPC ........... *G06K 9/2018* (2013.01); *B64D 43/00* (2013.01); *G01J 3/027* (2013.01); *G01J 3/26* (2013.01);
(Continued)

(58) Field of Classification Search
CPC .. G06K 9/2018; G06K 9/6267; G06K 9/6202; G06K 9/209; G06K 9/0063;
(Continued)

(56) References Cited

U.S. PATENT DOCUMENTS 5,357,263 A  10/1994  Fischer et al.
5,654,700 A   8/1997  Prata et al.
(Continued)

FOREIGN PATENT DOCUMENTS

CA   2615950 A1   1/2007

OTHER PUBLICATIONS

International Search Report and Written Opinion; dated Jun. 21, 2016 for PCT Application No. PCT/IL2016/050255.
(Continued)

*Primary Examiner* — John B Strege
(74) *Attorney, Agent, or Firm* — Xsensus LLP (57) ABSTRACT

Aircraft system and method detecting and present information relating to adverse airborne phenomena along an aircraft flight route. An imaging unit that includes an IR detector and a tunable spectral filter acquires IR images of the external environment, by acquiring wideband IR images when operating in a second mode. A data analysis unit detects and determines characteristics of adverse airborne phenomena in the environment based on at least the spectral signatures of environmental features in the acquired narrowband IR images. A display unit dynamically displays a visual representation of the detected adverse airborne phenomenon and its determined characteristics, overlaid onto a view of the external environment displayed to an operator of the aircraft. The visual representation may include variable visual attributes representing respective categories of characteristics of the detected adverse airborne phenomenon.

17 Claims, 8 Drawing Sheets

(51) Int. Cl.
- *H04N 5/33* (2006.01)
- *G01J 5/52* (2006.01)
- *G01J 3/32* (2006.01)
- *G01N 21/3504* (2014.01)
- *G01J 3/02* (2006.01)
- *B64D 43/00* (2006.01)
- *G01J 3/26* (2006.01)
- *G01J 3/28* (2006.01)
- *G06K 9/00* (2006.01)
- *G06K 9/62* (2006.01)
- *G01W 1/00* (2006.01)
- *G01N 21/17* (2006.01)

(52) U.S. Cl.
CPC ............ *G01J 3/2823* (2013.01); *G01J 3/32* (2013.01); *G01J 5/522* (2013.01); *G01N 21/3504* (2013.01); *G01W 1/08* (2013.01); *G06K 9/0063* (2013.01); *G06K 9/209* (2013.01); *G06K 9/6202* (2013.01); *G06K 9/6267* (2013.01); *H04N 5/33* (2013.01); *G01N 2021/1793* (2013.01); *G01N 2021/1795* (2013.01); *G01W 2001/003* (2013.01)

(58) Field of Classification Search
CPC .... G01J 3/2823; G01J 3/26; G01J 3/32; G01J 3/027; G01J 5/522; G01W 2001/003; G01W 1/08; B64D 43/00; H04N 5/33; G01N 2021/1795; G01N 2021/1793; G01N 21/3504
See application file for complete search history.

(56) References Cited

U.S. PATENT DOCUMENTS

| | | |
|---|---|---|
| 7,109,912 B1 | 9/2006 | Paramore et al. |
| 10,089,547 B2 * | 10/2018 | Shemesh ................. G01W 1/08 |
| 2007/0171397 A1 | 7/2007 | Halldorsson et al. |
| 2010/0231705 A1 | 9/2010 | Yahav et al. |
| 2013/0135470 A1 | 5/2013 | Prata et al. |

OTHER PUBLICATIONS

International Preliminary Report on Patentability; dated Jul. 11, 2017 for PCT Application No. PCT/IL2016/050255.

* cited by examiner

FIG. 11 ized by a large quantity of ash particles emitted and dispersed in the atmosphere. These micro-sized particles together with sand and dust can erode surfaces with which it comes into contact, and in more severe cases, can stall engines and compressors while penetrating into turbines and melting down rotating hot surfaces. Such events have led to major aircraft damages, and resulted in prolonged stoppages of aerial transportation.

DETECTION, CHARACTERIZATION AND PRESENTATION OF ADVERSE AIRBORNE PHENOMENA

BACKGROUND OF THE INVENTION

Aircrafts at takeoff, cruise and landing are prone to adverse airborne transparent or visible hazards. The source for these hazards is natural phenomenon, such as volcanic eruptions, atmospheric instability and jet streams. Most of the natural phenomena addressed here are not directly related to human activity. Yet, when it comes to aircrafts cruising at high altitudes, a wide spectrum of hazards is expected. These hazards range from bumpy flights, increased flight time, and higher fuel consumption to passenger injuries and aircraft crash risks.

Volcanic eruptions are worldwide phenomenon. Some active volcanoes are within the global flight routes of commercial aircrafts. A volcanic eruption is characterized by a large quantity of ash particles emitted and dispersed in the atmosphere. These micro-sized particles together with sand and dust can erode surfaces with which it comes into contact, and in more severe cases, can stall engines and compressors while penetrating into turbines and melting down rotating hot surfaces. Such events have led to major aircraft damages, and resulted in prolonged stoppages of aerial transportation.

Penetration of micro-particles into the aircraft cabin may risk the physical wellbeing of the aircraft passengers by adversely impacting the respiratory system, initiating lung diseases, or other health complications. A trail of volcanic ash is often accompanied with other more volatile materials, such as: acids and halogens. Sulfur dioxide ($SO_2$) and sulfuric acid ($H_2SO_4$) are two examples of eruption by-products that pose high risk to the aircrafts and to passengers. Sulfuric acid ($H_2SO_4$) is a highly corrosive acid, which can gradually damage various aircraft components. In contrast, halogens exposed to UV sunlight can form radicals, which harm the ozone as well as other materials.

Although volcanic ash clouds are frequently monitored by aerial instruments, there is a lack of real time, en-route, altitude specific information, which is needed for rapid assessment and maneuvering.

The presence of water ice particles is common at cruising flight altitudes. At cruising altitudes, water can exist as an undercooled liquid without freezing. When an aircraft impacts a cloud of undercooled water, the undercooled water will undergo a sudden freezing and form into ice. As a consequence, ice will accumulate on the aircraft body, which elevates both the weight and air drag of the aircraft.

Aircrafts may experience turbulent shear forces when encountering vertical air currents of an approximate scale of 100 m to 2 km. One of the physical mechanisms for such shear forces stems from convectively induced turbulences around clouds and thunderstorms. These turbulences are visible to the naked eye and to onboard radars, and thus may be easily avoided. Another source for instability occurs in clear atmospheric conditions and is referred to as "clear air turbulence (CAT)". It is assumed that man-made global warming partially contributes to these shear instabilities, which are expected to become more frequent in the impending future. Aircrafts encountering these invisible vertical shear forces may undergo sudden unpredictable movements and accelerations, resulting in the sensation of a "bumpy" flight, as well as potential injuries to aircraft crew members and passengers, and in extremes cases even fatalities. According to some estimates, aircrafts spend 3% of their cruising time in light intensity CATs and 1% of their cruising time in moderate CATs. Beyond their effect on passengers, CATs may also elicit structural damage of the aircraft and increase fuel consumption. To date, clear air turbulences are generally undetectable by onboard radars or satellites.

A current technology for turbulence detection is the enhanced X-band radar, with two main competitive systems: the Rockwell Collins WXR-700 series, and the Honeywell RDR-4 A/B series. These systems have two modes for detection of both wind shear and convective turbulence. However, based on market assessment of forward looking turbulence sensing systems, these systems were reported not to withstand expectations.

In recent years, Doppler LIDAR systems using phase information to determine vertical flow velocity of air lamella are under development, yet no commercial products are available. These systems rely on laser radiance emitted along the direction of flight route, monitoring the backscattering reflections of atmospheric molecules, such as carbon dioxide ($CO_2$) and oxygen ($O_2$). Two of the main disadvantages of LIDAR systems for CAT detection are narrow FOV, and limited laser power, resulting in limited detection range and angle. These drawbacks make it difficult for the pilot to obtain a complete image of the phenomenon and its extent. Lasers that operate at approximately 4-20 millijoules (mJ) allow for a detection range of about 5 miles, which is insufficient for risk assessment and decision making. Increasing the laser power, however, would lead to surplus weight as well as eye safety issues.

U.S. Pat. No. 7,109,912 to Paramore et al, entitled: "Weather radar hazard detection system and method", discloses an aircraft weather radar system that includes a radar antenna, optical aircraft sensors, a database, a processing device, and a cockpit display. The processing device receives radar returns from the radar antenna and environmental variables from the aircraft sensors, and detects storm system hazards using a cell height parameter for a cell. The cell height parameter is determined by determining a direction to the cell using the environmental variables, and a range to the cell using the radar returns. The storm system hazards are displayed using an iconal or textual representation. The hazards may include: overshooting tops, vertical development, hail, vaulted thunderstorms, air mass stability, or cell growth rate.

U.S. Pat. No. 5,357,263 to Fischer et al, entitled: "Display instrument for aircraft for showing the aircraft orientation, particularly the rolling and pitching position or the flight path angle", is directed to a head-up display of an aircraft which displays symbol features representative of the aircraft position in the exterior field of view of the pilot. The symbol features include a symbol stabilized in an earth-fixed manner for showing the true horizon position, as well as symbols representing the rolling angle, pitching angle, or flight path angle of the aircraft. A display of the attitude is generated by means of a reference symbol representing the aircraft and an information symbol which changes with respect to the reference symbol in its position and shape, and is dependent on the rolling angle and pitching angle or path angle.

U.S. Patent Application No. 2010/0231705 to Yahav et al, entitled: "Aircraft landing assistance", discloses an enhanced vision system for assisting aircraft piloting. An aircraft control operator sends flight instructions associated with an object of interest to a pilot wearing a head-mounted display (HMD). A visual representation of the flight instructions with the object of interest marked is generated, respective of a combined spatial and symbolic image viewed by the pilot on the HMD. The aircraft control operator receives from the pilot confirmation of the flight instructions by designating the marked object of interest on the combined spatial and symbolic image, where the designation is performed in conjunction with the line-of-sight of the pilot.

SUMMARY OF THE INVENTION

In accordance with one aspect of the present invention, there is thus provided an aircraft system for detecting and presenting information relating to adverse airborne phenomena along a flight route of the aircraft. The system includes a data acquisition unit, a data analysis unit, and a display unit. The data acquisition unit includes an imaging unit configured to acquire a plurality of infrared (IR) images of the external environment of the aircraft. The imaging unit includes an IR detector and a tunable spectral filter (TSF). The IR detector is configured to detect IR radiation. The TSF is configured to selectively transmit at least one IR wavelength band of incident light to the IR detector. When the imaging unit operates in a scanning mode, the TSF is tuned to transmit all detectable IR wavelength bands and the IR detector is configured to acquire wideband IR images of the environment. When the imaging unit operates in an investigation mode, the TSF is tuned to transmit selected IR wavelength bands and the IR detector is configured to acquire narrowband IR images of the environment, each of the narrowband IR images respective of a different IR spectral band. The data analysis unit is configured to receive and process the acquired wideband IR images, to detect at least one potential adverse airborne phenomenon in the environment. The data analysis unit is further configured to receive and process the acquired narrowband IR images, to verify and to determine at least one characteristic of a detected potential adverse airborne phenomenon, based on at least the spectral signatures of environmental features in the narrowband IR images. The display unit is configured to dynamically display a visual representation of the detected adverse airborne phenomenon and determined characteristic thereof, overlaid onto a view of the external environment displayed to an operator of the aircraft. The data acquisition unit may obtain information relating to the external environment from at least one of: a weather/climate forecast model; a 3D geographic model; a digital terrain elevation model (DTEM); a ground/satellite observation station; a bird migration information source; and/or another airborne platform. The detected adverse airborne phenomenon characteristic may include: a classification type, a location, a motion trajectory, a severity level and/or a technique for avoiding or mitigating the effects of the detected adverse airborne phenomenon. The data analysis unit may further compare the spectral signatures with predefined values or thresholds, to determine characteristics of the detected adverse airborne phenomenon. The visual representation may include a plurality of variable visual attributes, each of the visual attributes representing a respective category of the characteristics of the detected adverse airborne phenomenon. The visual attributes may include: at least one symbol; at least one color; at least one color attribute; at least one contour; at least one shape; at least one alphanumeric character; a text notification; a highlighting indication; a flashing visual attribute; and/or a varying visual attribute. The display unit may include a head-up display (HUD), a head-mounted display (HMD), and/or a display embedded within a wearable apparatus. The imaging unit may be further configured to operate in a calibration mode, in which the TSF is tuned to block radiation from both directions, and the TSF is positioned so as to reflect radiation emitted from a black-body surface at preselected temperatures toward the IR detector, allowing for offset and gain calibrations of the TSF. The data analysis unit may generate a contrast image from a plurality of narrowband images at different wavelength bands acquired by the imaging unit, and to determine a spectral signature from the contrast image. The adverse airborne phenomenon may include: a selected quantity of atmospheric particles; a selected quantity of volcanic ash particles; a selected quantity of acid or halogen molecules; a selected quantity of ice particles; a selected quantity of water droplets; a selected quantity of undercooled water droplets; a turbulence airflow; a vertical shear force; a convectively induced turbulence condition; a clear air turbulence (CAT) condition; and/or the presence of birds.

In accordance with another aspect of the present invention, there is thus provided a method for detecting and presenting information relating to adverse airborne phenomena along a flight route of an aircraft. The method includes the procedure of acquiring a plurality of infrared (IR) images of the external environment of the aircraft, using an imaging unit that includes: an IR detector, configured to detect IR radiation; and a tunable spectral filter (TSF), configured to selectively transmit at least one IR wavelength band of incident light to the IR detector. The method further includes the procedure of operating the imaging unit in a scanning mode, by tuning the TSF to transmit all detectable IR wavelength bands, and acquiring wideband IR images of the environment with the IR detector. The method further includes the procedure of receiving and processing the acquired wideband IR images, to detect at least one potential adverse airborne phenomenon in the environment. The method further includes the procedure of operating the imaging unit in an investigation mode, by tuning the TSF to transmit selected IR wavelength bands, and acquiring narrowband IR images of the environment with the IR detector, each of the narrowband IR images respective of a different IR spectral band. The method further includes the procedure of receiving and processing the acquired narrowband IR images, to verify and to determine at least one characteristic of a detected potential adverse airborne phenomenon, based on at least the spectral signatures of environmental features in the narrowband IR images. The method further includes the procedure of dynamically displaying a visual representation of the detected adverse airborne phenomenon and determined characteristic thereof, overlaid onto a view of the external environment displayed to an operator of the aircraft. The detected adverse airborne phenomenon characteristic may include: a classification type, a location, a motion trajectory, a severity level and/or a technique for avoiding or mitigating the effects of the detected adverse airborne phenomenon. The visual representation may include a plurality of variable visual attributes, each of the visual attributes representing a respective category of the characteristics of the detected adverse airborne phenomenon. The visual attributes may include: at least one symbol; at least one color; at least one color attribute; at least one contour; at least one shape; at least one alphanumeric character; a text notification; a highlighting indication; a flashing visual attribute; and/or a varying visual attribute. The method may further include the procedure of performing offset and gain calibrations of the TSF, by operating the imaging unit in a calibration mode, in which the TSF is tuned to block radiation from both directions, and the TSF is positioned so as to reflect radiation emitted from a black-body surface at preselected temperatures toward the IR detector. The IR image processing may include generating a contrast image from a plurality of narrowband images at different wavelength bands acquired by the imaging unit, where a spectral signature is determined from the contrast image. The adverse airborne phenomenon may include: a selected quantity of atmospheric particles; a selected quantity of volcanic ash particles; a selected quantity of acid or halogen molecules; a selected quantity of ice particles; a selected quantity of water droplets; a selected quantity of undercooled water droplets; a turbulence airflow; a vertical shear force; a convectively induced turbulence condition; a clear air turbulence (CAT) condition; and/or the presence of birds.

BRIEF DESCRIPTION OF THE DRAWINGS

The present invention will be understood and appreciated more fully from the following detailed description taken in conjunction with the drawings in which.

DETAILED DESCRIPTION OF THE EMBODIMENTS

The present invention overcomes the disadvantages of the prior art by providing a system and method for detecting and presenting information relating to adverse airborne phenomena along a flight route of an aircraft. The system includes data acquisition which collects data from various external and onboard data sources, including an infrared imaging unit with a Fabry-Pérot based tunable spectral filter that acquires wideband and narrowband IR images of the environment. The system further includes data analysis which involves a spectral analysis of the narrowband images at different wavelength bands for identifying adverse airborne phenomena. The system further includes dynamic display of a representation of the detected adverse airborne phenomena, overlaid over a scene view of the external environment, with variable symbols and other supplementary visual attributes depicted to indicate various characteristics of the detected phenomena. The adverse airborne phenomena may include, for example: volcanic ash clouds; dust; sand; airborne molecules and aerosols; other atmospheric particles; ice crystals or ice coated particles; super-cooled water particles; water droplets; uncooled water droplets; clear air turbulence (CAT); a CAT environmental condition; a turbulence airflow; a vertical shear force; a convectively induced turbulence environmental condition; wake vortices; and/or the presence of birds.

Figure 1:
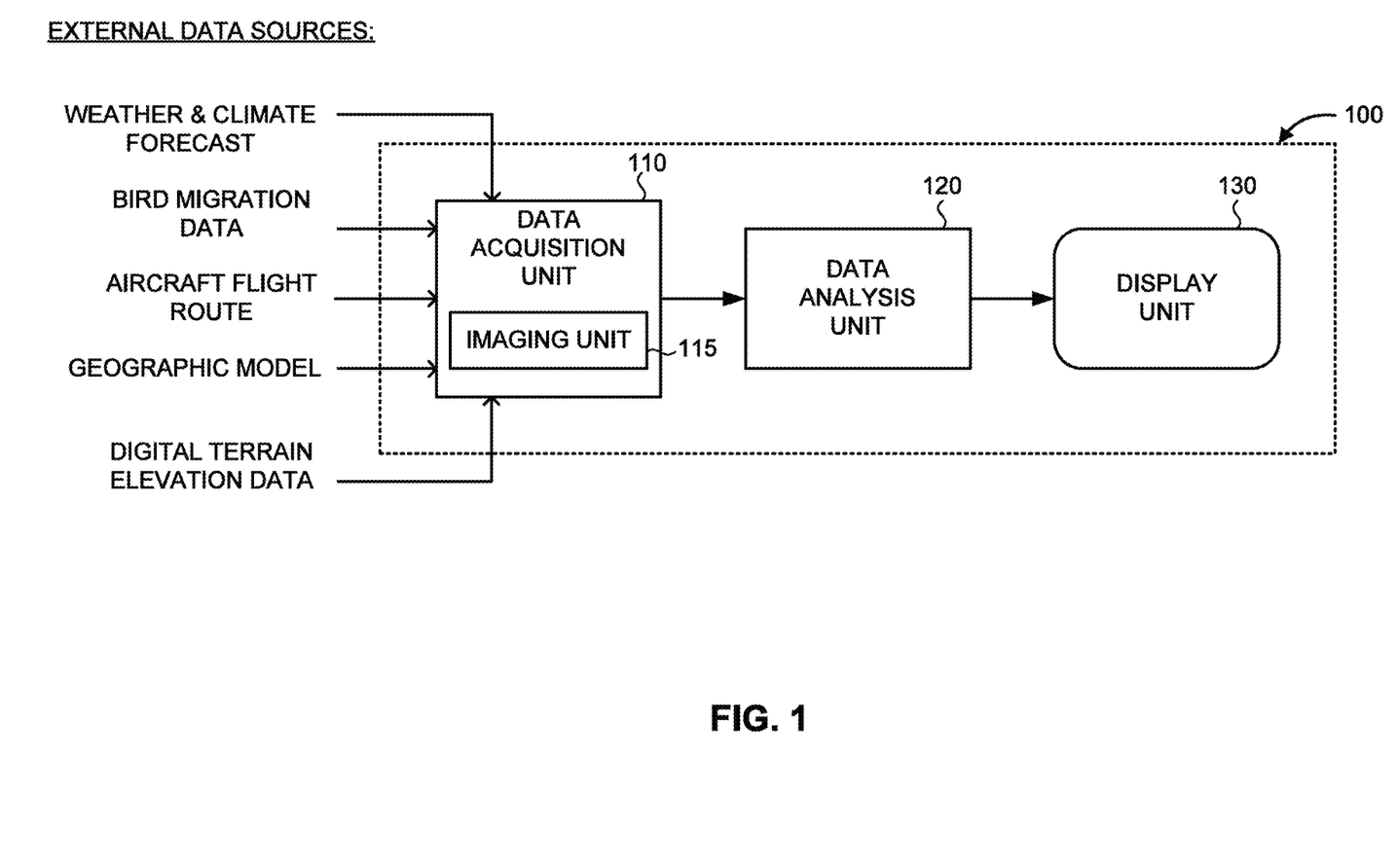
FIG. 1 is a schematic illustration of an aircraft system for detecting, characterizing, and presenting information relating to adverse airborne phenomena, constructed and operative in accordance with an embodiment of the present invention.

Reference is now made to FIG. 1, which is a schematic illustration of an aircraft system, generally referenced 100, for detecting, characterizing and presenting information relating to adverse airborne phenomena, constructed and operative in accordance with an embodiment of the present invention. System 100 includes three major sub-systems: data acquisition unit 110, data analysis unit 120, and display unit 130. Data acquisition unit 110 includes an imaging unit 115 that captures images of the external environment. Data acquisition unit 110 may also acquire additional data simultaneously from various external and on-board sources. The acquired data is transferred to analysis unit 120 in raw form or after undergoing initial processing. Data analysis unit 120 analyzes and evaluates the collection of data and the acquired images to identify different adverse airborne phenomena in the vicinity of the aircraft. Data analysis unit 120 may receive a digital representation of the images acquired by imaging unit 115, or may convert the raw image data into brightness temperature images. The image analysis may be based on a single image or multiple images. Data analysis unit 120 processes the data to determine further information, such as the severity level posed by the phenomenon to the aircraft and the aircraft passengers, the location of the phenomenon with respect to the aircraft, and the direction and velocity of the phenomenon. Data analysis unit 120 may also determine a predicted trajectory of the adverse airborne phenomenon with respect to the aircraft. Assessment of such characteristics may be based on thresholds, dynamic thresholds and/or lookup tables. To this end, data analysis unit 120 employs suitable algorithms for data extraction and data matching. Data analysis unit 120 also generates an image that provides a visual representation of the detected phenomena along with their associated characteristics.

Display unit 130 receives the analyzed data from data analysis unit 120 and provides a visual representation to the aircraft pilot (and/or other aircraft crew members), manifesting the most important characteristics of the detected adverse airborne phenomena. The characteristics may be displayed using symbology and by employing different visual attributes, such as different colors, shapes, contours, audible cues, text notifications, animations, and the like. Information of particular importance may be emphasized to the pilot, such as the concentration and estimated severity level of the phenomenon, the wind direction, and a predicted motion trajectory of the phenomenon. The characteristics may be transmitted to and stored at a ground station database. The stored data may be used for classification and evaluation of the detected adverse airborne phenomena, as well as generating a global mapping of these phenomena. The generating maps may then the be consulted for determining safe flight routes, helping to decrease aircraft fuel consumption and reduce the likelihood of encountering adverse airborne phenomena over the course of a flight.

Data acquisition unit 110 may collect on-line data from both external and on-board sources. For example, the collected data may include: weather or climate forecasts, bird migration data, aircraft flight routes, a three-dimensional (3D) geographic model or virtual globe, and digital terrain elevation data (DTED). The external data may be obtained, for example: from another airborne platform; from a ground or satellite observation station; from a geographic model or a digital terrain elevation map; from a volcanic ash advisory center (VAAC); from a publically available news source; and the like. The collected data is then processed by data analysis unit 120 to allow for the detection and characterization of adverse airborne phenomena, which may then be visual represented by display unit 130.

Figure 2:
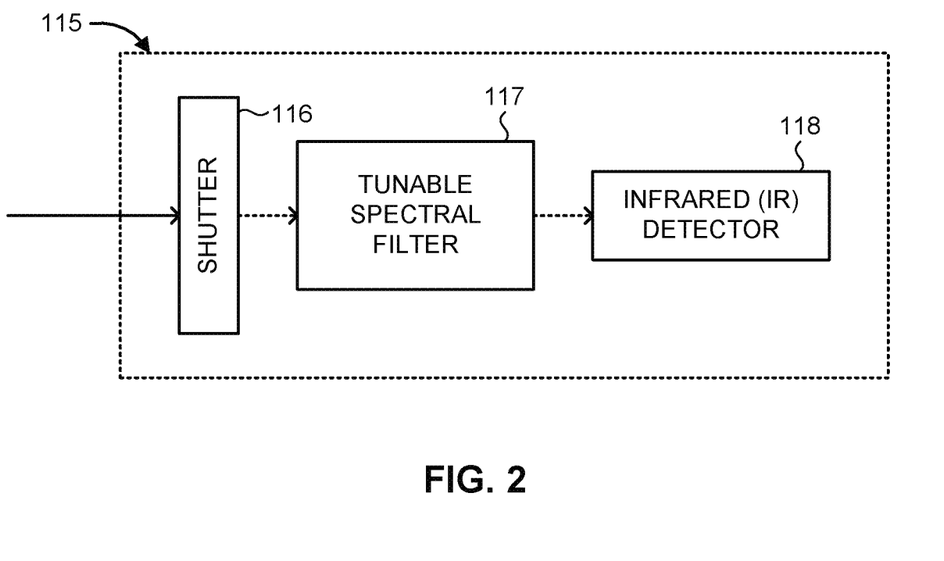
FIG. 2 is a schematic illustration of the imaging unit of the data acquisition unit of the system of FIG. 1, constructed and operative in accordance with an embodiment of the present invention.

Data acquisition unit 110 further includes an electro-optical based imaging unit 115. Reference is now made to FIG. 2, which is a schematic illustration of the imaging device 115 of the data acquisition unit 110 of the system 100 of FIG. 1, constructed and operative in accordance with an embodiment of the present invention. Imaging unit 115 includes an optical shutter 116, a tunable spectral filter (TSF) 117, and an infrared (IR) detector 118. TSF 117 and IR detector 118 are positioned behind optical shutter 116 along a common optical path. TSF 117 may be removed from the optical path if imaging unit 115 is intended to acquire full wideband images (in the IR spectral range). In order to acquire narrowband spectral images, TSF 117 is introduced into the optical path and tuned to the desired band. The precise location of TSF 117 along the optical path is design dependent, although usually positioned in front of a collimated beam.

IR detector 118 may be embodied by an uncooled microbolometer sensor with an active material such as vanadium-oxide (VOx). The uncooled sensor may be sensitive to infrared radiation at the long-wavelength IR region (e.g., between approximately 7 μm-14 μm). It is appreciated that detection in the infrared range is described herein for exemplary purposes, and that imaging unit 115 may generally include at least one sensor configured to acquire any form of electromagnetic radiation at any range of wavelengths (e.g., light in the visible or non-visible spectrum, ultraviolet, infrared, radar, microwave, RF, and the like).

Figure 3:
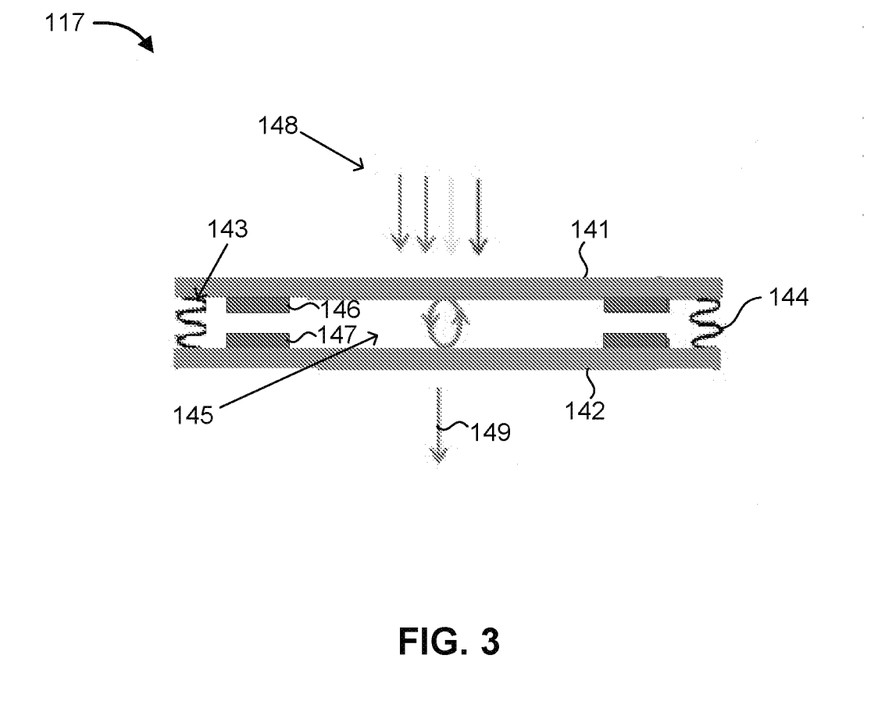
FIG. 3 is an illustration of the tunable spectral filter of the imaging unit of FIG. 2, constructed and operative in accordance with an embodiment of the present invention.

Reference is now made to FIG. 3, which is an illustration of the TSF 117 of the imaging unit 115 of FIG. 2, constructed and operative in accordance with an embodiment of the present invention. TSF 117 is based on a Fabry-Pérot interferometer, which includes two semi-transparent mirrors 141, 142, spring elements 143, 144, and actuators 146, 147. Each mirror 141, 142 includes a partially-reflective surface, which are aligned in parallel and separated by an optical gap defining a Fabry-Pérot cavity (referenced 145) in between. The optical gap may be composed of air or another medium through which light may pass through.

Incident light is reflected within the cavity 145 between mirrors 141 and 142, and light of a particular wavelength is transmitted from TSF 117, in accordance with the principles of a Fabry-Pérot interferometer. In particular, a broad spectrum input light beam (referenced 148) that includes a plurality of wavelengths ($\lambda_1 \ldots \lambda_n$) undergoes multiple reflections within cavity 145 between mirrors 141 and 142. The reflected beams interfere with each other, including constructive interference occurring when the beams are in phase, and destructive interference when the beams are out of phase. Whether the beams are in phase is a function of the inter-mirror or optical gap width, i.e., the separation distance between the two mirrors, as well as the light wavelength, the angle at which the light is incident on the mirror, and the refractive index of the separation medium. As a result, the light beam (referenced 149) exiting TSF 117 is a narrowband light beam having a selected wavelength ($\lambda_i$) that is a function of the width of optical gap 145.

Actuators 146, 147 and spring elements 143, 144 are operative to adjust the width of optical gap 145 in order to provide the desired outgoing wavelength. Spring elements 143, 144 are positioned between the parallel mirror surfaces along the outer periphery, and provide a counterbalancing force opposing forces acting to decrease the optical gap 145. Spring elements 143, 144 may be embodied by a thin strip of silicon, or another material that provides flexibility and support. Actuators 146, 147 are also disposed along the periphery of mirrors 112, 142 between the parallel surfaces, and are configured to apply a uniform force for moving one mirror relative to the other. In particular, each actuator 146, 147 applies an electromagnetic force which pushes or pulls mirror 142 (toward or away from mirror 141), while the respective spring element 143, 144 provides a resilient opposing mechanical force, thereby maintaining the spacing (optical gap width) between mirrors 141 and 142. The equilibrium between the electromagnetic force from actuators 146, 147 and the mechanical force from spring elements 143, 144 determines the location of mirrors 141 and 142, and correspondingly, the optical gap width, which defines the wavelength of exiting light beam 149.

Common types of actuators include electrostatic actuators (e.g., capacitors), piezoelectric actuators, and magnetic actuators. Considering for example electrostatic actuation, the optical gap is maximal when there is no actuation force, i.e., at zero voltage. By applying voltage between the actuators, the inter-mirror optical gap will tend to decrease. For electrostatic actuation, the applied force for decreasing the optical gap between the mirrors may be formulated as:

$$F_{electrostatic} = \frac{\varepsilon_0 A V^2}{2d^2}; \qquad \text{(Eqn. 1)}$$

where: $\varepsilon_0$ represents the vacuum permittivity constant; A represents the area of the actuator (actuation pad); V represents the applied voltage; and d represents the optical gap width.

Figure 4:
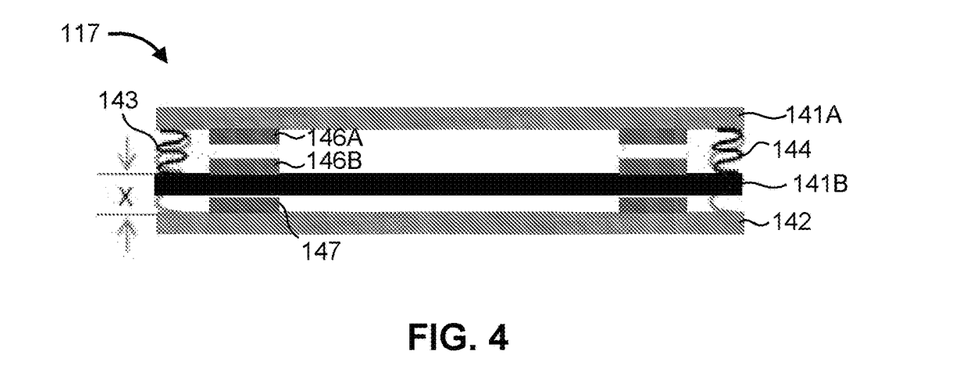
FIG. 4 is an illustration of the tunable spectral filter of FIG. 3 adjusting the inter-mirror separation distance to change the transmitted radiation wavelength, operative in accordance with an embodiment of the present invention.
Figure 5:
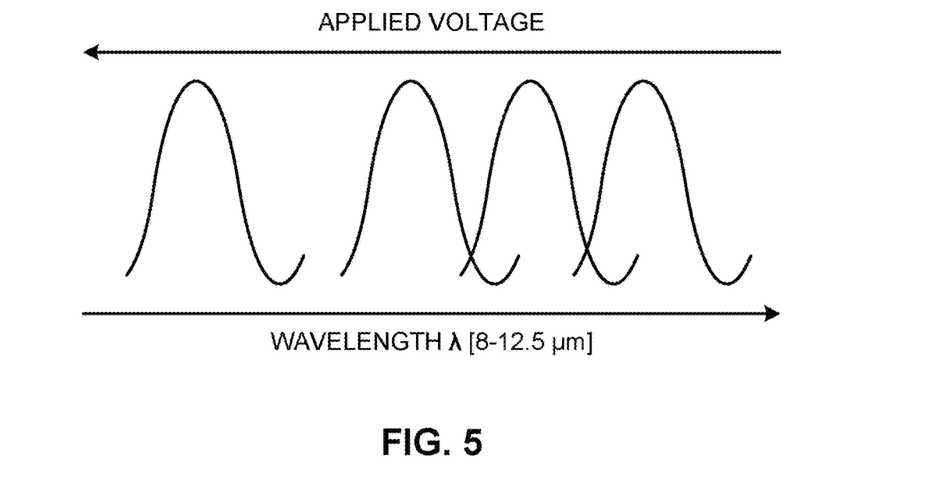
FIG. 5 is a graph showing narrow passbands as a function of applied voltage.

Reference is made to FIG. 4, which is an illustration of the tunable spectral filter 117 of FIG. 3 adjusting the inter-mirror separation distance to change the transmitted radiation wavelength, operative in accordance with an embodiment of the present invention. FIG. 4 depicts a change in the inter-mirror gap 145 as a result of applied actuation, where the gap width has decreased by the amount "x". As a result, the passing band of the emitted radiation 149 (i.e., the range of wavelength passing through TSF 117) will also be changed accordingly. Reference is made to FIG. 5, which is a graph showing narrow passbands as a function of applied voltage.

As with other optical elements, tunable filters may be subject to changes in ambient conditions such as temperature and humidity drifts. The changing ambient conditions can affect the response of the materials composing the tunable filter, and thereby influence the optical gap width 145 and the passband accuracy. Accordingly, TSF 117 may be calibrated at different ambient conditions in order to correct the fluctuations of the optical gap width resulting from different ambient conditions (discussed further below with reference to FIG. 6). Alternatively, imaging unit 115 may include a real-time correction circuit, configured to continuously obtain data relating to the position of mirrors 141, 142, based on which the inter-mirror gap can be adjusted as necessary. For example, electrodes deposited on the surfaces of each of mirrors 141, 142 may continuously measure the capacitance between the mirror surfaces, from which the inter-mirror gap width can be deduced, allowing for accurate monitoring and adjustment of the wavelength band of transmitted radiation 149.

The transmitted radiation through a Fabry-Perot based tunable spectral filter is given by the following equation:

$$T = \frac{1}{1 + F \cdot \sin^2\theta}; \quad \text{(Eqn. 2)}$$

where: F represents the contrast factor defined by the reflectance R of the semi-transparent mirrors, as follows:

$$F = \frac{4R}{(1-R)^2}; \quad \text{(Eqn. 3)}$$

and where the phase ($\theta$) for normal incidence of radiation is defined by: the refractive index of the optical gap (n); the optical gap width (d); and the wavelength ($\lambda$), as follows:

$$\theta = \frac{2\pi n d}{\lambda} \quad \text{(Eqn. 4)}$$

For full transmittance, the $\sin^2\theta$ factor will vanish, i.e., constructive standing waves are formed between the two semi-transparent mirrors of the filter. This is achieved when $\theta = \pi m$, where m represents an integer defining the order of the transmitting peaks.

Figure 6:
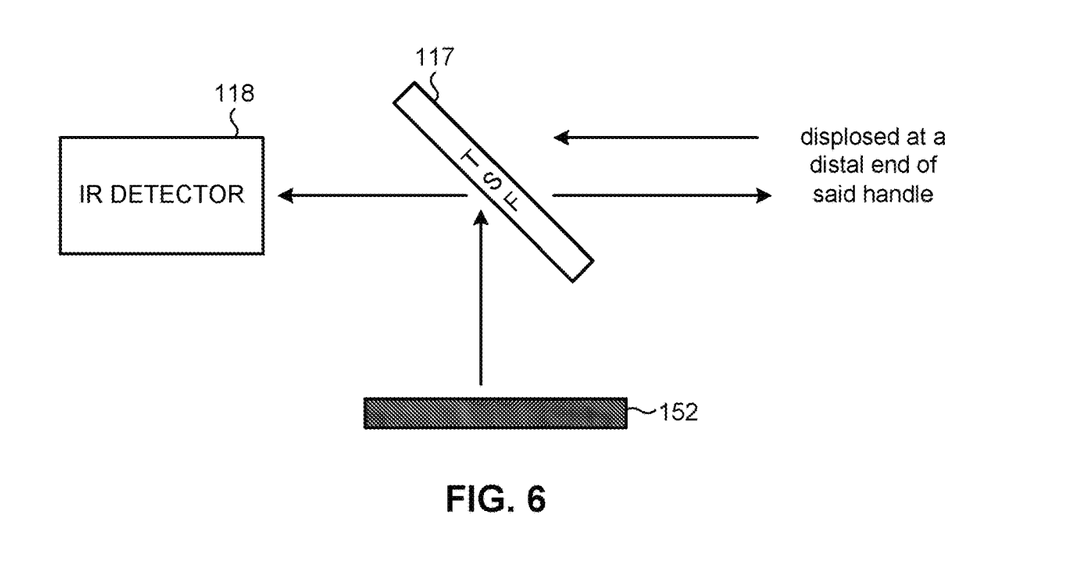
FIG. 6 is a schematic illustration of the image unit of FIG. 2 performing offset and gain calibration using a black body reference, operative in accordance with an embodiment of the present invention.
Figure 7A:
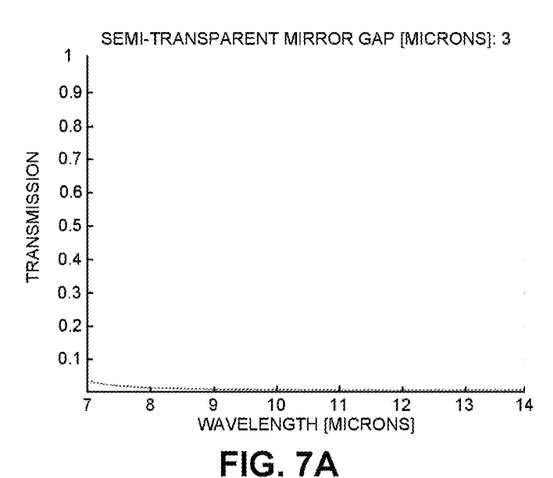
FIG. 7A is a graph of transmission as a function of wavelength for a tunable spectral filter operating at a closed mode, in accordance with an embodiment of the present invention.

TSF 117 is capable of operating in different operational modes. A first operational mode can be considered a "closed mode" or a "calibration mode". At a certain inter-mirror gap width, TSF 117 will block radiation at both directions, such that no radiation within the defined spectral range (e.g., LWIR) will pass through TSF 117 (i.e., any wavelength in the defined spectral range will be reflected). At this state it is possible to calibrate the offset and gain of IR detector 118. Reference is made to FIG. 6, which is a schematic illustration of the image unit 115 of FIG. 2 performing offset and gain calibration using a black-body reference surface, operative in accordance with an embodiment of the present invention. TSF 117 is inclined along an optical axis between the scene radiation and IR detector 118, and reflects radiation emitted from a black-body surface 152 at pre-selected temperatures, toward IR detector 118. In this manner, offset and gain calibrations can be performed as a function of a single or multiple black-body temperatures, respectively. Typically, such calibration is performed once every few minutes. The calibration may be performed for offset only, or for both offset and gain. The effect of self-radiation of TSF 117 may be minimized by thermally coupling TSF 117 through a heat-pipe (or another passive or active cooling mechanism) to the exterior ambient. This thermal coupling may be particularly effective for decreasing self-radiation at cruising altitudes where the temperatures are below zero Celsius degrees. Furthermore, in order to calibrate IR detector 118 to the temperatures in the imaged scene, black-body surface 152 may be thermally coupled to the exterior ambient using a heat pipe (or another passive or active cooling mechanism). Reference is made to FIG. 7A, which is a graph of transmission as a function of wavelength for a tunable spectral filter operating at a closed mode, in accordance with an embodiment of the present invention.

Figure 7B:
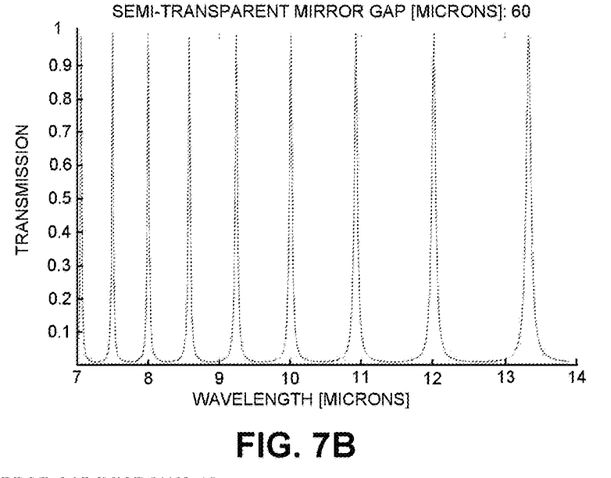
FIG. 7B is a graph of transmission as a function of wavelength for a tunable spectral filter operating at a high dynamic range mode, in accordance with an embodiment of the present invention.

Another operational mode of TSF 117 is a "high sensitivity mode" or "high dynamic range mode", in which multiple wavelengths in the defined spectral range (e.g., LWIR) are transmitted through TSF 117. In this mode, the optical gap width of TSF 117 is set so as to allow the formation of multiple transmitting peak orders (m=1, 2, . . . ), resulting in IR detector 118 acquiring images composed of multiple spatially separated wavebands. The simultaneous acquisition of multi-spectral waveband images ("wideband images") serves to increase the likelihood of an initial detection of an adverse airborne phenomenon (or lowering the detection time) since image data is acquired in a wide dynamic range, but at the expense of lowered spatial resolution (i.e., decreased precision in determining the location of the adverse airborne phenomenon). Reference is made to FIG. 7B, which is a graph of transmission as a function of wavelength for a tunable spectral filter operating at a high dynamic range mode, in accordance with an embodiment of the present invention.

Figure 7C:
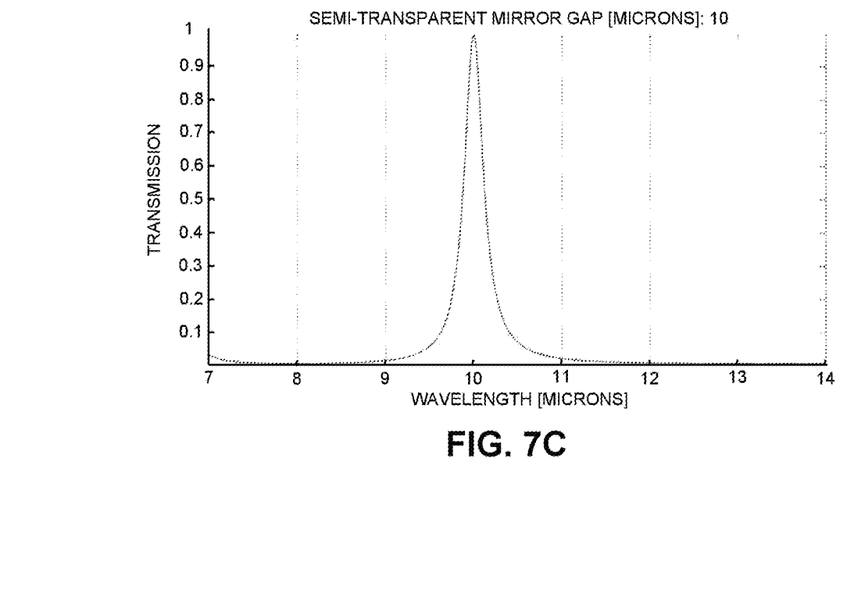
FIG. 7C is a graph of transmission as a function of wavelength for a tunable spectral filter operating at a high resolution mode, in accordance with an embodiment of the present invention.

A further operational mode of TSF 117 is a "high resolution mode", in which TSF 117 passes through a single wavelength band in the defined spectral range (e.g., LWIR), such that IR detector 118 captures a single spectral waveband image ("narrowband image") at a time. This mode allows for determining the location of an adverse airborne phenomenon in the imaged scene with a higher degree of precision (i.e., higher spatial resolution), but at the expense of not detecting other adverse airborne phenomena having a characteristic spectral response in a different spectral band. Reference is made to FIG. 7C, which is a graph of transmission as a function of wavelength for a tunable spectral filter operating at a high resolution mode, in accordance with an embodiment of the present invention.

The "high dynamic range" mode and the "high resolution" mode are generally complementary, and TSF 117 may generally repeatedly switch between these modes in an iterative manner to enhance the overall process of detecting and characterizing multiple adverse airborne phenomena. In particular, the high dynamic range mode of TSF 117 may also be considered as a "scanning mode", in which imaging unit 115 is directed to detect all potential adverse airborne phenomena by acquiring wideband images in all available (IR) wavelength bands. Correspondingly, the high resolution mode of TSF 117 can be considered an "investigation mode" in which imaging unit 115 is directed to acquire only narrowband images in selected (IR) wavelength bands (i.e., one or more discrete spectral bands), in order to determine further information and more accurate information relating to a potential adverse airborne phenomenon previously detected in the scanning mode.

For example, if data acquisition unit 110 receives minimal preliminary information about potential adverse airborne phenomenon to be encountered along the flight route of the aircraft, then imaging unit 115 may operate initially in a "scanning mode" (or high dynamic range mode) so as to scan the scene for various adverse airborne phenomena with equal probability. When the presence of a specific adverse airborne phenomenon is detected, such as by imaging unit 115 operating in scanning mode and/or by information obtained from an external data source, then imaging unit 115 may be directed to operate in an "investigation mode" (or high resolution mode) in order to concentrate on collecting further information on the detected phenomenon (such as its spatial location). For example, imaging unit 115 may tentatively detect a potential adverse airborne phenomenon when operating in a scanning operational mode, and then positively verify (and obtain further characteristics of) the tentatively detected adverse airborne phenomenon when operating in an investigation operational mode. Investigation mode operation allows for enhanced data collection and analysis, in order to decrease the likelihood of false alarms (i.e., falsely detecting an adverse airborne phenomenon when one is not actually present). Imaging unit 115 may subsequently go back to operating in scanning mode, followed by another investigation mode after detecting a new adverse airborne phenomenon, repeating iteratively as necessary. In this manner, the detectability level (i.e., the quality of the detections, such as the amount and the accuracy of information obtained) is increased, and the detection time (or number of "missed detections") is decreased. Increasing detectability may also be achieved by scanning selected spectral bands (of relevant potential adverse airborne phenomena) more frequently, thereby effectively increasing the signal to noise ratio (SNR), and/or by focusing on a selected region of interest (ROI) in the imaged scene.

Figure 8:
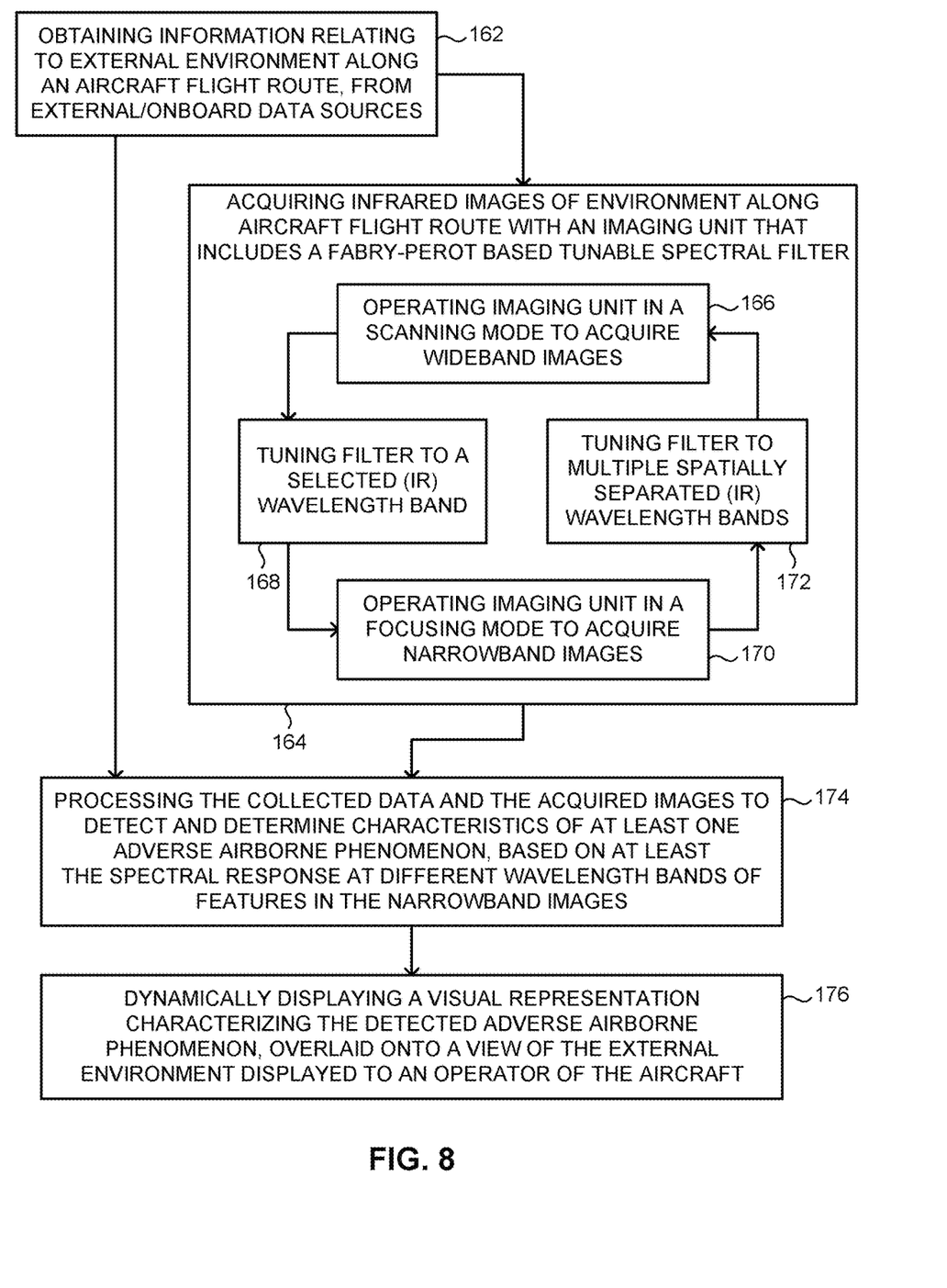
FIG. 8 is a flow diagram of a method for detecting, characterizing, and presenting information relating to adverse airborne phenomena, operative in accordance with an embodiment of the present invention.

Reference is now made to FIG. 8, which is a flow diagram of a method for detecting, characterizing, and presenting information relating to adverse airborne phenomena, operative in accordance with an embodiment of the present invention. In procedure 162, information relating to the external environment along an aircraft flight route is obtained from external or onboard data sources. Referring to FIG. 1, data acquisition unit 110 obtains data relating to the environment in the vicinity of system 100, such as weather or climate forecasts, bird migration data, aircraft flight routes, a 3D geographic model or virtual globe, and/or digital terrain elevation data.

In procedure 164, infrared images of the environment along the aircraft flight route is acquired with an imaging unit that includes a Fabry-Perot based TSF. Referring to FIGS. 1 and 2, data acquisition unit 110 includes an imaging unit 115 that includes TSF 117 and IR detector 118. Imaging unit 115 acquired wideband and narrowband infrared images of the environment in the vicinity of system 100. In particular, in sub-procedure 166, imaging unit 115 operates in a scanning mode to acquire wideband images. When imaging unit 115 operates in a scanning mode or high dynamic range mode, the optical gap width of TSF 117 is set to transmit multiple IR wavelengths such that IR detector 118 captures multiple images of spatially separated (IR) wavelength bands. If for example it is desired to focus on a specific adverse airborne phenomenon detected in a scanning mode so as to obtain the spatial location or other information, as well as to improve the accuracy of the obtained information, imaging unit 115 may be directed to operate in an investigation mode or a high resolution mode. Accordingly, TSF 117 is tuned to one or more selected discrete spectral bands (sub-procedure 168) associated with the specific adverse airborne phenomenon. As a result, IR detector 118 captures narrowband (IR) images in the selected wavelength bands, allowing imaging unit 115 operating in the high resolution mode (sub-procedure 170) to determine further characteristics of the specific adverse airborne phenomenon, such as its location. Subsequently, TSF 117 may be re-tuned to pass through multiple wavelengths to enable wideband imaging (sub-procedure 172), and imaging unit 115 returns to scanning mode operation for detecting new adverse airborne phenomena. Accordingly, imaging unit 115 iteratively switches between scanning mode operation and investigation mode operation as required, to enhance the overall detection and characterization capabilities. Imaging unit 115 may also undergo recurrent calibration, such as using a black-body surface 152 set at pre-selected temperatures (FIG. 6), to allow for offset and gain calibrations.

The images acquired by imaging unit 115 are transferred to data analysis unit 120 for processing and detection and characterization of adverse airborne phenomena. The sequence of filter tuning, image acquisition, and image transfer to data analysis unit 120 is repeated continuously for each of the selected narrowbands in which imaging unit 115 operates. The number of acquired images depends on various parameters, such as the sensitivity of IR detector 118, the concentration of the airborne phenomenon to be detected, and the like.

In procedure 174, the collected data and the acquired images are processed to detect and determine characteristics of at least one adverse airborne phenomenon, based on at least the spectral response at different wavelength bands of features in the narrowband images. Referring to FIG. 1, data analysis unit 120, which is synchronized with IR detector 118 and TSF 117, receives the acquired IR images and other collected data from data acquisition unit 110. The images are stored for further processing and data extraction. In particular, data analysis unit identifies the spectral response of different regions or environmental features present in the narrowband images. The unique spectral response at different wavelength bands is known as a "spectral signature". Each airborne phenomenon is characterized by a unique spectral signature. Accordingly, imaging unit 115 generally acquires multiple narrowband images at different spectral bands, so as to enable the determination of a characteristic spectral signature and to decrease the false alarm rate (FAR).

Figure 9:
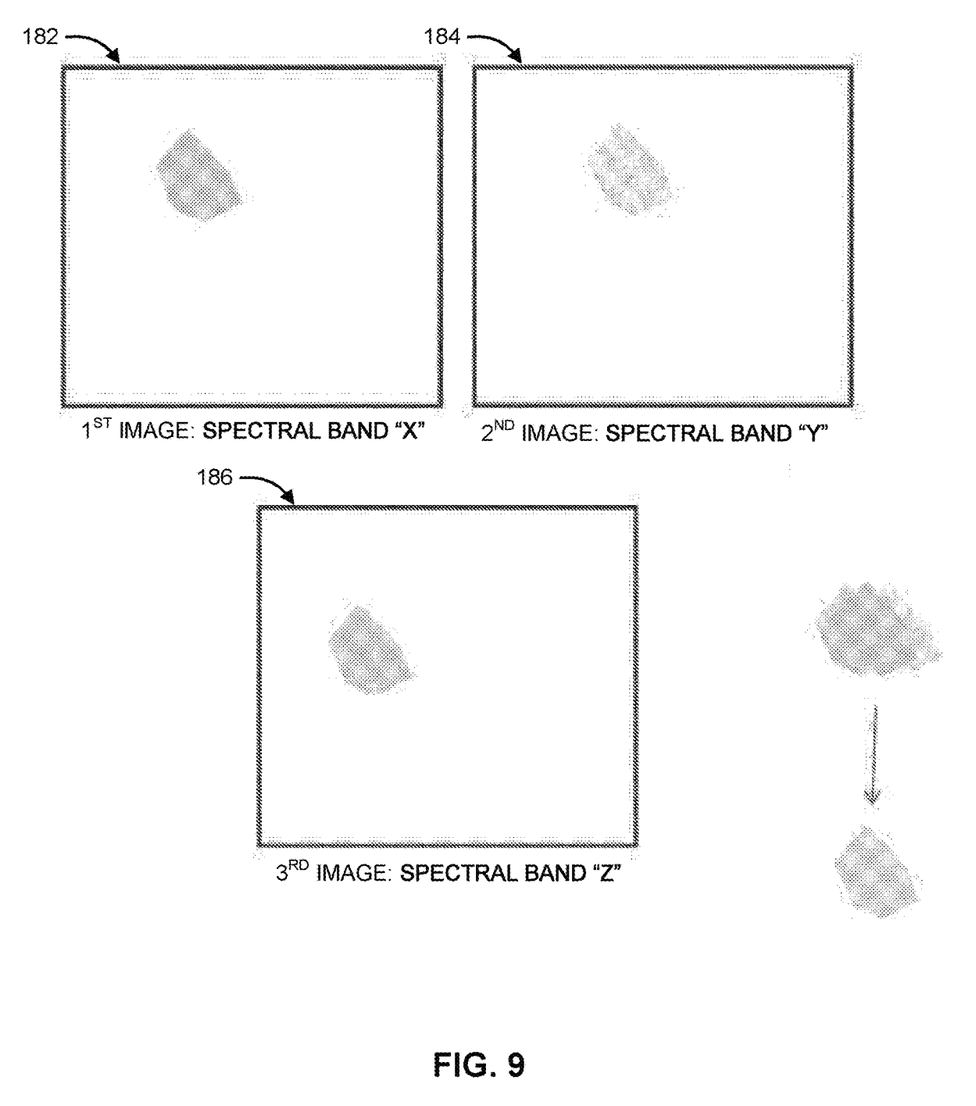
FIG. 9 is an illustration of an exemplary spectral signature extracted from multiple narrowband images acquired at different spectral bands, operative in accordance with an embodiment of the present invention.

The spectral signature of the airborne phenomena depends on the nature of the interaction of the LWIR photons with the particles or physical elements that make up the particular phenomenon. Reference is made to FIG. 9, which is an illustration of an exemplary spectral signature extracted from multiple narrowband images acquired at different spectral bands, operative in accordance with an embodiment of the present invention. Image 182 is acquired at a first spectral band "X", image 184 is acquires at a second spectral band "Y", and image 186 is acquired at a third spectral band "Z". Each image 182, 184, 186 is characterized by a particular spectral response at a different wavelength band. When these spectral responses at different spectral bands are processed together, a unique spectral signature is obtained. This spectral signature forms the basis for the detection and identification of adverse airborne phenomena.

For particles at the molecular level, the type of interaction (between the LWIR photons and the environmental particles) is usually absorption. For example, considering silicon dioxide ($SO_2$) and ozone ($O_3$), there are two distinct absorption bands associated with $SO_2$ that appear in the LWIR range: at approximately 7.3 μm and 8.6 μm. Accordingly, data analysis unit 120 may examine the spectral response at each of these bands (or both) to identify the characteristic spectral response of silicon dioxide.

In the case of micro-sized particles, the type of interaction is usually a combination of absorption, scattering and transmission. For example, volcanic ash clouds of aged ash particles may have a characteristic particle diameter of approximately 3-10 μm. For detecting such ash particles, a contrast image may be generated from two narrowband images acquired at two different wavelengths, e.g., 11 μm and 12 μm. Volcanic ash particles have a distinct wavelength-dependent refractive index (usually opposite to that of water), which may be easily apparent in the background of the processed contrast image.

Another physical mechanism which can be utilized for detecting certain phenomena is the reststrahlen effect, in which radiation within a narrow wavelength band cannot propagate within a particular medium due to a change in refractive index concurrent with the specific absorption band of the medium. As a result, a reststrahlen band radiation will undergo strong reflection from that medium. The reststrahlen effect is responsible for a unique spectral signature at a wavelength of 8.2 μm which is associated with quartz. Therefore, monitoring this particular wavelength can provide an indication of the presence and concentration of quartz, which is one of the volcanic ash constituents.

Figure 10:
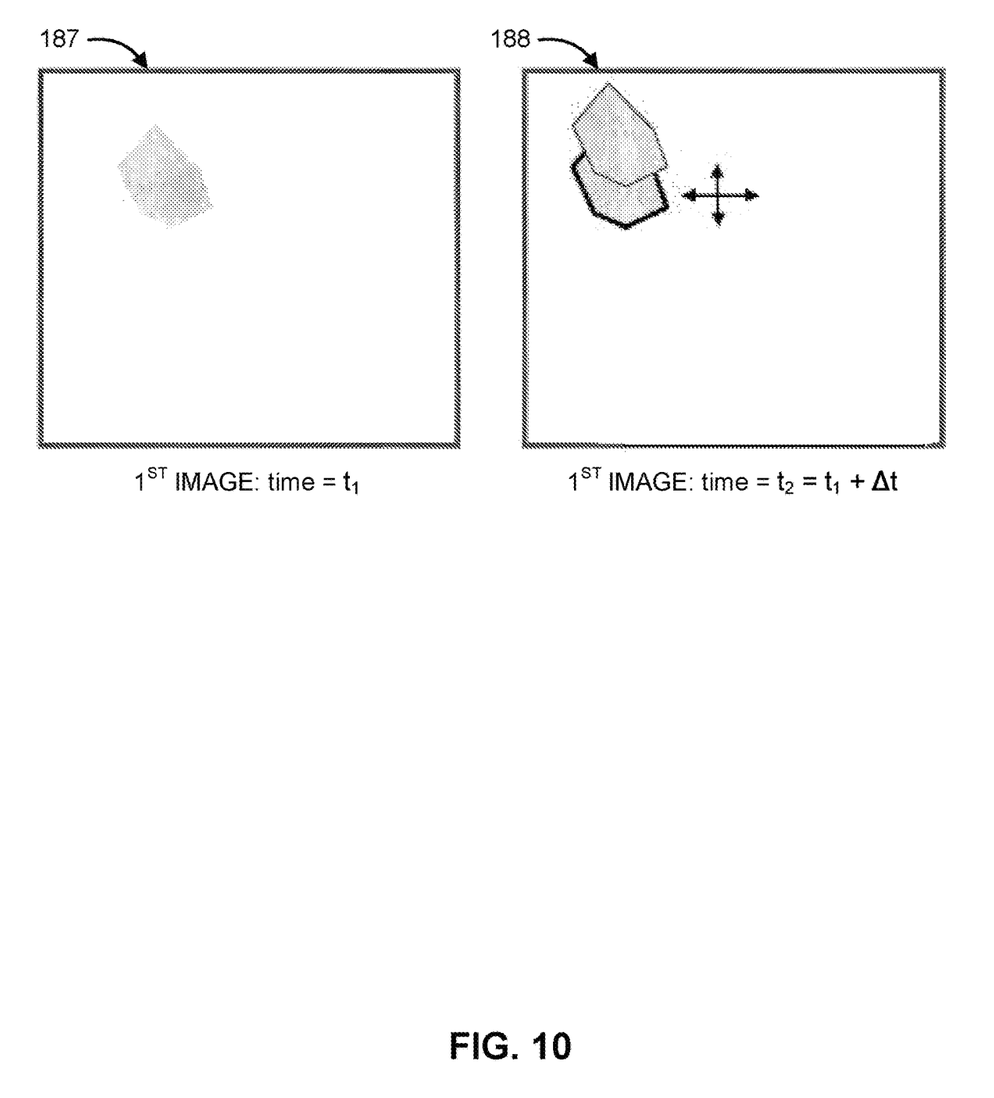
FIG. 10 is an illustration of an exemplary spectral response extracted from a narrowband image changing over time, operative in accordance with an embodiment of the present invention.

The identified spectral signature may also take into account changes in the spectral response over time. Reference is made to FIG. 10, which is an illustration of an exemplary spectral response extracted from a narrowband image changing over time, operative in accordance with an embodiment of the present invention. Image 187 is acquired (at a particular spectral band) at a first time instance "$t_1$", while image 188 represents image 187 acquired at a later time instance "$t_2$"=$t_1$+Δt. Image 187 depicts a particular spectral response of an environmental feature present in the captured image, while image 188 depicts the same spectral response shifting location, for example indicating a shift in the location of the particular feature between time "$t_1$" and time "$t_2$".

Data analysis unit 120 may compare the multi-source processed data with known values and thresholds in order to obtain various characteristics associated with a detected adverse airborne phenomenon, such as an estimate of severity level (e.g., the level of danger posed to the aircraft and/or the aircraft passengers by the phenomenon). Data analysis unit 120 may also determine relevant characteristics from the identified spectral signature of the phenomenon. The determined characteristics may include the location of the phenomenon (e.g., arrival direction, the extent and volume), a motion trajectory of the phenomenon (e.g., including its velocity, possible pathways), a classification type or categorization of the phenomenon (e.g., based on weather type, severity level, and the like). The determined characteristics (and the detection of the phenomenon itself) may be associated with a probability metric representing a level of confidence value. Data analysis unit 120 may also determine possible countermeasures or techniques for avoiding or minimizing the adverse effects arising from a detected phenomenon.

An operator of system 100 may establish or adjust the threshold levels for detection of an adverse airborne phenomenon, and may apply adaptive thresholds in real-time during the aircraft flight. The detection threshold levels may be selected manually, or established based on default or dynamically changing criteria. For example, a clear-air turbulence (CAT) phenomenon may have a different subjective impact on the pilot as compared to the aircraft passengers. If the pilot considers the current CAT detection thresholds to be too high, such as after encountering a particular CAT event, then the pilot may reclassify CATs for detection along the current aircraft flight route to include only CATs characterized with lower thresholds. In this manner, data analysis unit 120 will avoid unnecessary detections of CATs considered to be "light intensity".

Data analysis unit 120 further generates an image of detected adverse airborne phenomena, which then overlaid onto a (wideband) image of the external environment which is displayed to the pilot (or other aircraft crew member) via display unit 130, enabling the pilot to easily perceive the extent of the airborne phenomenon with respect to the field of view.

In procedure 176, a visual representation characterizing the detected adverse airborne phenomenon is dynamically displayed overlaid onto a view of the external environment displayed to an operator of the aircraft. Referring to FIG. 1, display unit 130 receives an image representation of adverse airborne phenomena detected by data analysis unit and presents the image representation to an operator of system 100. The displayed image may be a wideband video image, which is updated in real-time in accordance with changes in the displayed airborne phenomena, and which is conformed to a view of the external scene. Display unit 130 may be at least partially transparent (i.e., a "see-through display"), such that the viewer can simultaneously observe images or other visual content superimposed onto the display along with a view of the external environment through the display, providing the viewer with situational awareness. Display unit 130 may be embodied by a head-mounted display (HMD) that includes a display embedded within a wearable apparatus worn by the operator, such as a helmet, a headband, a visor, spectacles, goggles, and the like. Alternatively, display unit 130 may be another type of display, such as: a head-up display (HUD), e.g., embedded in the aircraft cockpit; a portable or hand-held display; a display screen of a mobile computing device; and the like.

The wideband image of the detected phenomena superimposed on display unit 130 may be based on the infrared images captured by imaging unit 115, or by other cameras or detectors coupled with data acquisition unit 110. The detected adverse airborne phenomena and their associated characteristics may be displayed visually in various forms, such as image objects, graphics, symbols, animations, and the like.

Figure 11:
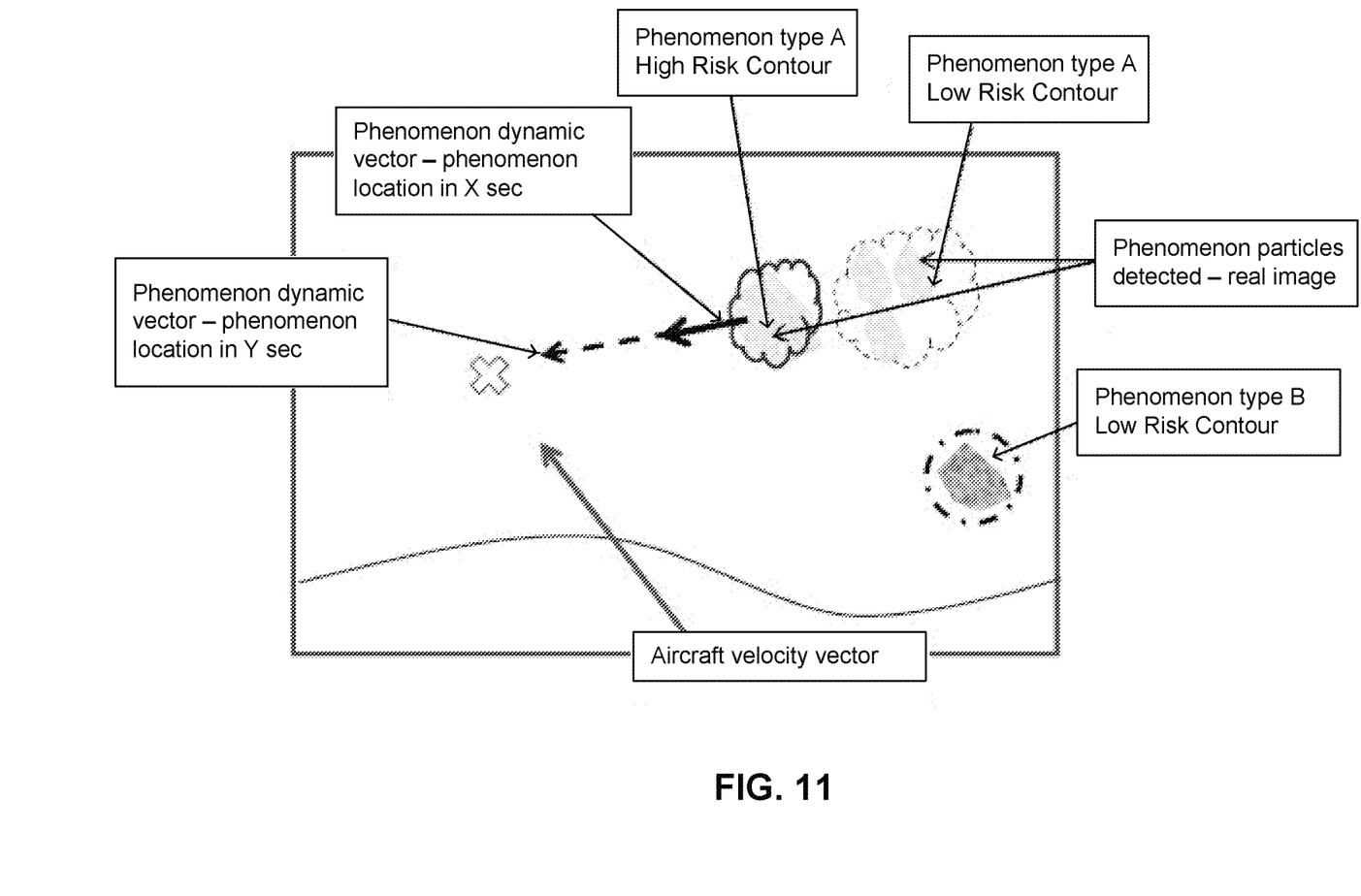
FIG. 11 is a schematic illustration of a dynamic display of detected adverse airborne phenomena, constructed and operative in accordance with an embodiment of the present invention.

Reference is made to FIG. 11, which is a schematic illustration of a dynamic display of detected adverse airborne phenomena, constructed and operative in accordance with an embodiment of the present invention. The visual representation of the detected adverse airborne phenomenon is superimposed onto a view of the external environmental within the field of view of the pilot. The displayed image includes an indication of the location of the detected phenomena, as well as additional information such as a dynamic vector representing the motion trajectory of the airborne phenomenon, and the severity level. The phenomenon characteristics are presented synthetically using symbols, text, colors, audible cues, animation, magnification, and the like.

The visual representation of the detected phenomena may include variable visual attributes representing different categories or classifications of the adverse airborne phenomena and their characteristics. For example, a first detected phenomenon characterized with a "high severity" may be visually depicted using a first variation of at least one visual attribute, such as: a particular shape (e.g., a triangle), a particular color (e.g., red), a particular contour (e.g., bold or high intensity outline), and/or a particular text notification ("warning—high severity"). Correspondingly, a second detected phenomenon characterized with a "medium severity" may be visually depicted using a second variation of the visual attribute(s), such as: a different shape (e.g., a diamond), a different color (e.g., yellow), a different contour (e.g., italics or medium intensity bolded outline), and/or a different text notification ("warning—medium severity"). Finally, a third detected phenomenon characterized with a "low severity" may be visually depicted using a third variation of the visual attribute(s), such as: another different shape (e.g., a circle), another different color (e.g., green), another different contour (e.g., regular font or low intensity outline), and/or a particular text notification ("clear—low severity).

The presence of an adverse airborne phenomenon may be indicated using a solid or dashed contour line. A blinking contour may provide an alert of a particular phenomenon, with the blinking frequency indicating the severity level. Different visual symbols allow the viewer to distinguish one adverse airborne phenomenon form another, such that multiple phenomena can be displayed simultaneously. Physical characteristics of the adverse airborne phenomenon may be emphasized in different ways. For example, the concentration of the adverse airborne phenomenon may be represented using colors, and a reference color bar may be presented alongside the displayed image to assist interpretation. The velocity (speed and direction) of the adverse airborne phenomenon may be depicted using arrows, where the arrow size represents the speed. Similarly, a relevant symbol bar may be presented on the displayed image to assist interpretation of the various symbols. A further technique for visually depicting the severity level classification (e.g., direct impact on the aircraft and/or the passengers) of adverse airborne phenomena utilizes the transparency level of the symbol, where for example, phenomena associated with higher severity levels will be depicted as opaque (lesser transparency) whereas those associated with lower severity levels are depicted as transparent. Other visual attribute indications may include: relative size (e.g., increasing or decreasing the size of a symbol); a color-related parameter or color attribute (e.g., changing the brightness, hue, saturation, luminance, radiance of a symbol); emphasizing or highlighting a portion of the symbol; omitting a portion of the symbol; changing the type of symbol entirely; and the like.

The displayed visual representation facilitates the decision making of the pilot for avoiding or otherwise mitigating the effects of the detected adverse airborne phenomenon along the flight route of the aircraft. Additional relevant information obtained from data acquisition unit 110 and/or other aircraft systems may also be taken into consideration for determining an optical flight maneuver (e.g., to adjust the current flight route) or other suitable course of action.

Referring back to FIG. 10, the inter-image analysis performed by data analysis unit 120 may provide additional time-dependent information relating to the adverse airborne phenomenon. Such information may be displayed as predicted characteristics, such as time-dependent concentration and position. For example, the position of the adverse airborne phenomenon while the aircraft passes nearby may be depicted using animation showing the routes and positions of both the aircraft and the phenomenon according to its current velocity. Such a visual representation may further assist the pilot in determining a suitable course of action in order to safely avoid the airborne phenomenon.

While certain embodiments of the disclosed subject matter have been described, so as to enable one of skill in the art to practice the present invention, the preceding description is intended to be exemplary only. It should not be used to limit the scope of the disclosed subject matter, which should be determined by reference to the following claims.

The invention claimed is:

1. An aircraft system for detecting and presenting information relating to adverse airborne phenomena along a flight route of the aircraft, the system comprising:
   a data acquisition unit, comprising an imaging unit configured to acquire a plurality of infrared (IR) images of the external environment of said aircraft, said imaging unit comprising:
   an IR detector, configured to detect IR radiation; and
   a tunable spectral filter (TSF), configured to selectively transmit at least one IR wavelength band of incident light to said IR detector,
   wherein when said imaging unit operates in a scanning mode, said TSF is tuned to transmit all detectable IR wavelength bands, and said IR detector is configured to acquire wideband IR images of said environment,
   and wherein when said imaging unit operates in an investigation mode, said TSF is tuned to transmit selected IR wavelength bands, and said IR detector is configured to acquire narrowband IR images of said environment, each of said narrowband IR images respective of a different IR spectral band,
   a data analysis unit, configured to receive and process the acquired wideband IR images to detect at least one potential adverse airborne phenomenon in said environment, said data analysis unit further configured to receive and process the acquired narrowband IR images to verify and to determine at least one characteristic of a detected potential adverse airborne phenomenon, based on at least the spectral signatures of environmental features in said narrowband IR images; and a display unit, configured to dynamically display a visual representation of the detected adverse airborne phenomenon and determined characteristic thereof, overlaid onto a view of said external environment displayed to an operator of said aircraft.

2. The system of claim 1, wherein said data acquisition unit is configured to obtain information relating to said external environment from at least one data source selected from the list consisting of:
   a weather/climate forecast model;
   a three-dimensional (3D) geographic model;
   a digital terrain elevation model (DTEM);
   a ground/satellite observation station;
   a bird migration information source;
   another airborne platform; and
   any combination of the above.

3. The system of claim 1, wherein said characteristic of the detected adverse airborne phenomenon is selected from the list consisting of:
   a classification type of said detected adverse airborne phenomenon;
   a location of said detected adverse airborne phenomenon;
   a motion trajectory of said detected adverse airborne phenomenon;
   a severity level of said detected adverse airborne phenomenon; and
   at least one technique for avoiding or mitigating the effects of said detected adverse airborne phenomenon.

4. The system of claim 1, wherein said data analysis unit is further configured to compare said spectral signatures with predefined values or thresholds, to determine characteristics of said detected adverse airborne phenomenon.

5. The system of claim 1, wherein said visual representation comprises a plurality of variable visual attributes, each of said visual attributes representing a respective category of the characteristics of said detected adverse airborne phenomenon.

6. The system of claim 5, wherein said visual attributes is selected from the list consisting of:
   at least one symbol; at least one color;
   at least one color attribute; at least one contour;
   at least one shape;
   at least one alphanumeric character; a text notification;
   a highlighting indication; a flashing visual attribute;
   a varying visual attribute;
   and any combination of the above.

7. The system of claim 1, wherein said display unit comprises at least one display selected from the list consisting of:
   a head-up display (HUD);
   a head-mounted display (HMD); and
   a display embedded within a wearable apparatus.

8. The system of claim 1, wherein said imaging unit is further configured to operate in a calibration mode, in which said TSF is tuned to block radiation from both directions, and said TSF is positioned so as to reflect radiation emitted from a black-body surface at preselected temperatures toward said IR detector, allowing for offset and gain calibrations of said TSF.

9. The system of claim 1, wherein said data analysis unit is configured to generate a contrast image from a plurality of narrowband images at different wavelength bands acquired by said imaging unit, and to determine a spectral signature from said contrast image.

10. The system of claim 1, wherein said adverse airborne phenomenon is selected from the list consisting of:
   a selected quantity of atmospheric particles;
   a selected quantity of volcanic ash particles;
   a selected quantity of acid or halogen molecules;
   a selected quantity of ice particles;
   a selected quantity of water droplets;
   a selected quantity of undercooled water droplets;
   a turbulence airflow;
   a vertical shear force;
   a convectively induced turbulence condition; a clear air turbulence (CAT) condition;
   the presence of birds; and any combination of the above.

11. A method for detecting and presenting information relating to adverse airborne phenomena along a flight route of an aircraft, the method comprising the procedures of:
   acquiring a plurality of infrared (IR) images of the external environment of said aircraft, using an imaging unit comprising: an IR detector, configured to detect IR radiation; and a tunable spectral filter (TSF), configured to selectively transmit at least one IR wavelength band of incident light to said IR detector;
   operating said imaging unit in a scanning mode, by tuning said TSF to transmit all detectable IR wavelength bands, and acquiring wideband IR images of the environment with said IR detector;
   receiving and processing the acquired wideband IR images, to detect at least one potential adverse airborne phenomenon in said environment;
   operating said imaging unit in an investigation mode, by tuning said TSF to transmit selected IR wavelength bands, and acquiring narrowband IR images of the environment with said IR detector, each of said narrowband IR images respective of a different IR spectral band;
   receiving and processing the acquired narrowband IR images, to verify and to determine at least one characteristic of a detected potential adverse airborne phenomenon, based on at least the spectral signatures of environmental features in said narrowband IR images; and
   dynamically displaying a visual representation of the detected adverse airborne phenomenon and determined characteristics thereof, overlaid onto a view of said external environment displayed to an operator of said aircraft.

12. The method of claim 11, wherein said characteristic of the detected adverse airborne phenomenon is selected from the list consisting of:
   a classification type of said detected adverse airborne phenomenon;
   a location of said detected adverse airborne phenomenon;
   a motion trajectory of said detected adverse airborne phenomenon;
   a severity level of said detected adverse airborne phenomenon; and
   at least one technique for avoiding or mitigating the effects of said detected adverse airborne phenomenon.

13. The method of claim 11, wherein said visual representation comprises a plurality of variable visual attributes, each of said visual attributes presenting a respective category of the characteristics of said detected adverse airborne phenomenon.

14. The method of claim 13, wherein said visual attributes is selected from the list consisting of: at least one symbol;
   at least one color;
   at least one color attribute;
   at least one contour;
   at least one shape;
   at least one alphanumeric character;
   a text notification;
   a highlighting indication;
   a flashing visual attribute;
   a varying visual attribute; and
   any combination of the above.

15. The method of claim 11, further comprising the procedure of performing offset and gain calibrations of said TSF, by operating said imaging unit in a calibration mode, in which said TSF is tuned to block radiation from both directions, and said TSF is positioned so as to reflect radiation emitted from a black-body surface at preselected temperatures toward said IR detector.

16. The method of claim 11, wherein said procedure of processing the IR images comprises generating a contrast image from a plurality of narrowband images at different wavelength bands acquired by said imaging unit, wherein a spectral signature is determined from said contrast image.

17. The method of claim 11, wherein said adverse airborne phenomenon is selected from the list consisting of:
   a selected quantity of atmospheric particles; a selected quantity of volcanic ash particles;
   a selected quantity of acid or halogen molecules;
   a selected quantity of ice particles;
   a selected quantity of water droplets;
   a selected quantity of undercooled water droplets;
   a turbulence airflow;

a vertical shear force;
a convectively induced turbulence condition;
a clear air turbulence (CAT) condition;
the presence of birds; and any combination of the above.

* * * * *